United States Patent [19]

Bender et al.

[11] Patent Number: 4,686,231

[45] Date of Patent: Aug. 11, 1987

[54] INHIBITION OF 5-LIPOXYGENASE PRODUCTS

[75] Inventors: Paul E. Bender, Cherry Hill, N.J.; Don E. Griswold, North Wales; Nabil Hanna, Berwyn; Henry M. Sarau, Hatfield, all of Pa.

[73] Assignee: SmithKline Beckman Corporation, Philadelphia, Pa.

[21] Appl. No.: 856,927

[22] Filed: Apr. 28, 1986

Related U.S. Application Data

[63] Continuation-in-part of Ser. No. 808,395, Dec. 12, 1985.

[51] Int. Cl.$^4$ .............. C07D 403/30; C07D 233/66; C07D 401/00; C07D 405/00

[52] U.S. Cl. .............................. 514/333; 548/315; 548/337; 546/256; 546/278; 514/341; 514/398; 514/400; 514/396

[58] Field of Search .............. 548/315, 337; 546/256, 546/278; 514/333, 341, 398, 400, 396

[56] References Cited

U.S. PATENT DOCUMENTS

| | | | |
|---|---|---|---|
| 3,772,441 | 11/1973 | Lombardino | 548/315 |
| 3,929,807 | 12/1975 | Fitzi et al. | 548/315 |
| 3,940,486 | 2/1976 | Fitzi et al. | 548/315 |
| 3,997,552 | 12/1976 | Buchel | 548/337 |
| 4,159,338 | 6/1979 | Cherkofsky et la. | 548/315 |
| 4,175,127 | 11/1979 | Bender et al. | 548/315 |
| 4,182,769 | 1/1980 | Cherkofsky et al. | 548/315 |
| 4,190,666 | 2/1980 | Cherkofsky et al. | 548/315 |
| 4,199,592 | 4/1980 | Cherkofsky et al. | 548/315 |
| 4,308,277 | 12/1981 | Ferrini et al. | 548/315 |
| 4,461,770 | 7/1984 | Ferrini et al. | 548/315 |

FOREIGN PATENT DOCUMENTS

845074 11/1977 Belgium .............................. 548/315

OTHER PUBLICATIONS

Lombardino et al., *J. Med. Chem.* 17(11), 1182-1188 (1974).
Bender et al., *J. Med. Chem.*, 28, 1169-1177 (1985).
Zauer et al., *Chem. Bir.* 106, 1628-1636 (1973).
Tanino et al., Bulletin of the *Chemical Society of Japan*, 45, 1474-1480 (1972).
White et al., *J. Org. Chem.*, 29, 1926-1930 (1964).
Lantos et al., *J. Med. Chem.*, 27(1), 72-75 (1984).

*Primary Examiner*—Henry R. Jiles
*Assistant Examiner*—Robert C. Whittenbaugh
*Attorney, Agent, or Firm*—Nancy S. Mayer; Stuart R. Suter; Alan D. Lourie

[57] ABSTRACT

Novel compounds, compositions and pharmaceutical a method of inhibiting the 5-lipoxygenase pathway in an animal in need thereof which comprising administering an effective, 5-lipoxygenase pathway inhibiting amount of a 4,5-diaryl-2(substituted)-imidazole or a pharmaceutically acceptable salt thereof.

37 Claims, No Drawings

INHIBITION OF 5-LIPOXYGENASE PRODUCTS

CROSS REFERENCE TO RELATED APPLICATIONS

This application is a continuation-in-part of Ser. No. 808,395 filed Dec. 12, 1985, which is pending.

BACKGROUND OF THE INVENTION

This invention relates to novel compounds, pharmaceutical compositions and a method of inhibiting the 5-lipoxygenase pathway of arachidonic acid metabolism in an animal in need thereof which comprises administering to such animal an effective, 5-lipoxygenase inhibiting amount of a 4,5-diaryl-2(substituted) imidazole or a pharmaceutically acceptable salt thereof.

Lombardino et al., U.S. Pat. No. 3,772,441, issued Nov. 13, 1973 disclose compounds of the formula

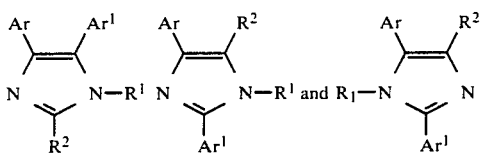

and the pharmaceutically acceptable acid addition salts thereof,

Ar and $Ar^1$ are each selected from furyl, thienyl, pyridyl, phenyl and substituted phenyl, wherein said substituents are selected from fluoro, chloro, bromo, and $C_{1-4}$ alkoxy;

$R^1$ is selected from H or $C_{1-4}$ alkyl; and $R^2$ is selected from trifluoro methyl, $C_{1-4}$ alkyl, furyl, thienyl, pyridyl, and substituted phenyl wherein said substituents are selected from fluoro, chloro, bromo, or $C_{1-4}$ alkoxy. Lombardino et al. disclose that such compounds are antiinflammatory agents based on their activity in the carrageenan rat foot adena test. Such test is useful for detecting compounds which are cyclooxygenase inhibitors, but is of no known utility in detecting or suggesting compounds which are inhibitors of the 5-lipoxygenase pathway. Lombardino et al. also state that compounds are useful as antiarthritic agents but there is no further statement as to how such antiarthritic activity was determined. Such a blanket statement of antiarthritic activlity does not disclose that such compounds have 5-lipoxygenase pathway inhibition.

Lombardino et al., J. Med. Chem. 17(11), 1182–1188(1974) disclose compounds of the formula

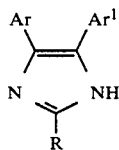

wherein Ar and $Ar^1$ are selected from methoxyphenyl, 4-ethoxyphenyl, 2-pyridyl and 4-halophenyl; and R is selected from 4-halophenyl, $CF_3$, phenyl and 4-methoxyphenyl. Lombardino et al. disclose that some of such compounds have antiinflammatory activity in the carrageenan rat paw edema test which is useful for detecting compounds which are inhibitors of cyclooxygenase but is of no known utility of detecting or suggesting compounds which are inhibitors of the 5-lipoxygenase pathway.

Bender et al., J. Med. Chem., 28, 1169–1177 (1985), disclose compounds of the formula

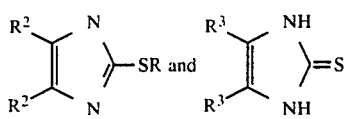

wherein R is methyl or ethyl, $R^1$ is H, methyl or ethyl, $R^2$ is 4-methoxyphenyl, and $R^3$ is 4-methyoxyphenyl, 4-bromophenyl or 3-fluorophenyl. Bender et al. also disclose that some of such compounds have antiarthritic activity in the rat adjuvant-induced arthritis assay and immuno-regulatory activity mouse subliminal oxazolone-induced contact sensitivity assay. The adjuvant-induced arthritis assay is useful for detecting compounds which are cyclooxygenase inhibitors, but is of no known utility for detecting or suggesting compounds which are inhibitors of the 5-lipoxygenase pathway. The mouse subliminal oxazolone induced arthritis assay is useful for detecting compounds which are immunostimulants but is of no known utility for detecting or suggesting compounds which are inhibitors of the 5-lipoxygenase pathway.

Cherkofsky et al., U.S. Pat. No. 4,190,666, issued Feb. 26, 1980 disclose compounds of the formula

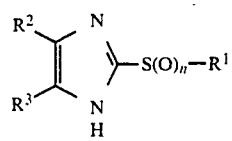

wherein:

n is 0, 1 or 2;

$R_1$ is $C_{1-6}$ alkyl or polyhalo $C_{1-6}$ alkyl; and $R_2$ and $R_3$ are independently selected from monosubstituted phenyl wherein said substituent is selected from $C_{1-4}$ alkoxy, chloro or fluoro.

Cherkofsky et al. also disclose that such compounds have antiinflammatory activity as determined by the established adjuvant-induced arthritis assay in rats; immunoregulatory effects as determined by the non-established adjuvant-induced arthritis assay in rats; and analgesic activity as determined by the phenylquinone writhing test. As stated above, the established adjuvant-induced arthritis test is of no known utility in detecting or suggesting cmpounds with 5-lipoxygenase pathway inhibiting activity. The non-established adjuvant arthritis assay is useful for detecting compounds with cyclooxygenase inhibiting activity but is of no known utility for detecting or suggesting compounds with 5-lipoxygenase pathway inhibiting activity. The phenylquinone writhing test is useful for detecting compounds with cyclooxygenase inhibiting activity but is of no known utility for detecting or suggesting compounds with 5-lipoxygenase pathway inhibiting activity.

Zauer et al., Chem Ber, 106, 1628–1636(1973), disclose 4,5-bis(p-chlorophenyl)-2-(methylthio)imidazole and 4,5-bis(p-methoxyphenyl)-2-methylimidazole. There is no disclosure in Zaver, et al. regarding any biological activity of such compounds.

Ferrini et al., U.S. Pat. No. 4,308,277, issued Dec. 29, 1981, disclose compounds of the formula

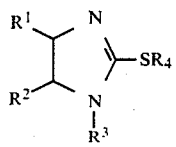

wherein:
R₁ and R₂ are independently selected from thienyl or mono-substituted phenyl wherein said substituent is selected from lower alkoxy and halo;
R³ is lower alkyl; and
R⁴ is lower alkyl.

Ferrini, et al. state that such compounds have immunoregulatory, antiinflammatory, antithrombolic and/or antinociceptive activity as exhibited by their activity in the Kaoline paw oedema assay in normal rats and adjuvant-induced arthritic assay in rats, the phenyl-p-benzoquinone-induced writhing assay in mice, the iv administered acetic acid induced writing assay in rats, the pulmonary embolism assay in rabbits, and an assay of inhibition of prostaglandin synthesis from arachidonic acid by spermatocystic enzymes in cattle. The Kaolin paw oedema assay is useful for detecting compounds which are cyclooxygenase inhibitors, but is of no known utility in detecting compounds which are inhibitors of the 5-lipoxygenase pathway. As stated above, the phenyl-p-benzoquinone and adjuvant-induced arthritis assays are of no known utility in detecting or suggesting compounds which are inhibitors of the 5-lipoxygenase pathway. The iv-administered acetic acid induced writing assay in rats is useful for detecting compounds which are cyclooxygenase inhibitors. The assay of inhibition of prostaglandin synthesis induced by spermatocystic enzymes is useful for detecting compounds which are inhibitors of the cyclooxygenase pathway. None of the acetic acid induced writhing assay, pulmonary embolism assay or the prostaglandin synthesis assay of any known utility are useful for detecting or suggesting compounds which are inhibitors of the 5-lipoxygenase pathway.

Dupont, Belgium Patent Application No. 845,074, published Nov. 2, 1977, disclose compounds of the formula

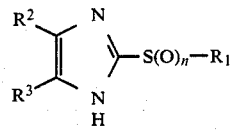

wherein:
n is 0, 1 or 2;
R₁ is mono or polyhalo C₁₋₄ alkyl or C₁₋₄ alkyl; and
R₂ and R₃ are independently selected from mono-substituted phenyl wherein said substituents are selected from C₁₋₄ alkoxy, chloro or fluoro.

Dupont discloses that such compounds have antiinflammatory and immunoregulatory properties based on their activity in the non-established and established adjuvant-induced arthritis assay in rats, both of which, as stated above, have no known utility in detecting or suggesting compounds which are inhibitors of the 5-lipoxygenase pathway.

Janino et al., *Bulletin of the Chemical Society of Japan*, 45, 1474–1480 (1972), and White et al., *J. Org. Chem.*, 29, 1926–1930 (1964), disclose 2,4,5-tri(p-chlorophenyl)imidazole. There is no disclose in either reference regarding any biological activity of this compound.

Cherkofsky et al., U.S. Pat. No. 4,182,769, issued Jan. 8, 1980, disclose compounds of the formula

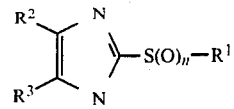

wherein:
n is 0, 1 or 2;
R₁ is C₁₋₆ alkyl and mono- and polyhalo C₁₋₄ alkyl; and
R₂ and R₃ are independently selected from monosubstituted phenyl wherein said substituent is selected from C₁₋₄ alkoxy, Cl or F. Cherkofsky et al. state that such compounds have antiinflammatory activity and analgesic activity as indicated by the adjuvant-induced arthritis assay in rats, which, as stated above, is of no known utility in detecting compounds which are inhibitors of the 5-lipoxygenase pathway.

Ferrini et al., U.S. Pat. No. 4,461,770, issued July 24, 1984, disclose compounds of the formula

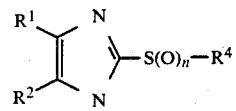

wherein at least one of the radicals R₁ and R₂ is a substituted or unsubstituted heteroaryl group and the other is a substituted or unsubstituted aryl group; R₃ is H or lower alkyl, n is 0, 1 or 2, and R₄ is substituted or unsubstituted aliphatic hydrocarbon radical, and pharmaceutically usable salts thereof. Ferrini et al. also disclose that such compounds have anti-inflammatory, antinociceptive and/or anti-thrombotic activity as well as an inhibitory action on prostaglandin synthesis based on their effects in the Kaolin paw oedema test, the carrageenan paw edema test, the phenyl-p-benzoquinone induced writhing assay in mice; the arachidonate induced embolic assay in rabbit lung and the in vitro inhibition of prostaglandin synthesis from arachidonic acid assay. As stated above, none of such assay systems have any known utility for detecting or suggesting compounds which are inhibitors of the 5-lipoxygenase pathway.

Cherkofsky et al., U.S. Pat. No. 4,159,338, issued June 26, 1979, disclose compounds of the formula

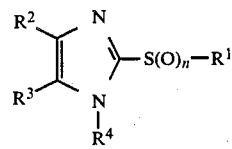

wherein:
n is 0, 1 or 2;
R₁ is polyfluoro C₁₋₂ alkyl;

$R_2$ and $R_3$ are independently selected from 2-thienyl, 3-thienyl, 3-pyridyl, 2-furyl or monosubstituted phenyl wherein said substituent is selected from $C_{1-4}$ alkoxy, Cl or F and $R_4$ is H, and pharmaceutically acceptable acid addition salts thereof.

Cherkofsky, et al. also disclose that such compounds have antiinflammatory, antiarthritic and/or analgesic activity based on their activity in the established adjuvant induced arthritis assay in rats and in the phenylquinone writhing test in mice. As stated above, none of such assays are of any known utility in detecting or suggesting compounds which are inhibitors of the 5-lipoxygenase pathway.

Bender et al., U.S. Pat. No. 4,175,127, issued Nov. 20, 1979, disclose compounds of the formula

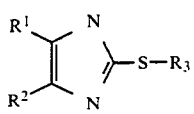

wherein:

$R_3$ is H, $C_{1-6}$ alkyl or mono- or polyhalo $C_{1-4}$ alkyl; and $R^1$ and $R^2$ are the same or different, but one of which always being pyridyl, are pyridyl or monosubstituted phenyl wherein said substituent is selected from lower alkoxy, chloro, fluoro or bromo.

Bender, et al. also disclose that when $R_3$ is H, such compounds are useful only as intermediates, and when $R_3$ is other than H, such compounds have potent antiarthritic activity based on their activity in the adjuvant-induced polyarthritis assay in rats which, as stated above, is of no known utility for detecting or suggesting compounds which are inhibitors of the 5-lipoxygenase pathway.

Fitzi et al., U.S. Pat. No. 3,940,486, issued Feb. 24, 1976, and Fitzi et al. U.S. Pat. No. 3,929,807, issued Dec. 30, 1975, disclose compounds of the formula

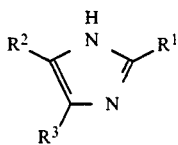

wherein:

$R_1$ is halo-substituted phenyl; and one of the groups of $R_2$ and $R_3$ represents phenyl which is optionally substituted by halo or lower alkoxy and the other is a 6-membered heteroaromatic ring, and salts of such compounds.

Fitzi et al. also disclose that such compounds have antiinflammatory, antinociceptive and antipyretic action based on their activity in the Bolus alba oedema test in rats; the phenyl-p-benzoquinone-induced writhing assay in mice, and yeast-induced fever assay in rats. As stated above, such assays have no known utility in detecting or suggesting compounds with 5-lipoxygenase pathway inhibiting activity.

Lantos et al., *J. Med. Chem.*, 27(1), 72–75(1984), disclose 4-(4-methyoxyphenyl)-5-(4-pyridyl)-2-thione-imidazole and 4-(4-fluorophenyl)-5-(4-pyridyl)-2-thione-imidazole as intermediates.

Cherkofsky et al., U.S. Pat. No. 4,199,592, issued Apr. 12, 1980, disclosed compounds of the formula

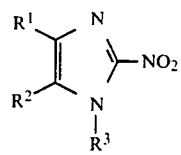

wherein:

$R_3$ is H; and $R_1$ and $R_2$ are independently selected from pyridyl, thienyl or monosubstituted phenyl wherein said substituent is selected from chloro, fluoro or $C_{1-4}$ alkoxy.

Cherkofsky, et al. also disclose that such compounds have antiinflammatory, antiarthritic and/or analgesic activity based on their activity in the established adjuvant-induced arthritis assay in rats and the phenylquinone induced writhing assay in mice. As stated above, none of such assays either disclose or suggest comounds with 5-lipoxygenase inhibiting activity.

SUMMARY OF THE INVENTION

This invention relates to a compound of the formula

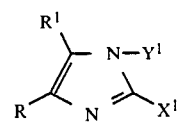

Formula (IA)

wherein:

$X^1$ is NHCN or $NH_2$;

$R^1$ and R are independently selected from pyridyl or monosubstituted phenyl wherein said substituent is selected from halo or $C_{1-4}$ alkoxy; and $Y^1$ is H or CN; provided that when $X^1$ is $NH_2$, $Y^1$ is CN, and when $X^1$ is NHCN, $Y^1$ is H;

or a pharmaceutically acceptable salt thereof.

This invention also relates to a pharmaceutical composition comprising an effective, non-toxic 5-lipoxygenase pathway inhibiting amount of a compound of Formula (IA), or a pharmaceutically acceptable salt thereof, and a pharmaceutically acceptable carrier or diluent.

This invention also relates to a method for treating rheumatoid arthritis in an animal in need thereof which comprises administering to such animal an effective, non-toxic 5-lipoxygenase pathway inhibiting amount of Formula (IA).

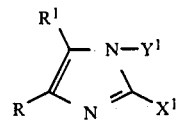

Formula (IA)

This invention also relates to a method of treating a 5-lipoxygenase pathway mediated disease in an animal, including a mammal, in need thereof, provided that such animal is in need of treatment of a 5-lipoxygenase pathway mediated disease other than, or in addition to, rheumatoid arthritis, which comprises administering to such animal an effective, non-toxic 5-lipoxygenase pathway inhibiting amount of a compound of the formula

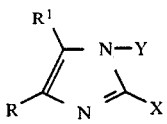

Formula (I)

wherein:
X is S, S(O)nR², NHCN, polyhalo C$_{1-4}$ alkyl, or 4-halophenyl;
n is 0, 1 or 2;
R² is selected from H, C$_{1-6}$ alkyl, or mono- or polyhalo C$_{1-4}$ alkyl;
R and R¹ are independently selected from pyridyl or monosubstituted phenyl wherein said substituent is selected from halo or C$_{1-4}$ alkoxy; provided that when R and/or R¹ are pyridyl, R² is other than C$_{1-6}$ alkyl, tetrahaloethyl or C$_{1-4}$ perhaloalkyl; and
Y is H, CN, or C$_{1-4}$ alkyl; provided that when X is NH$_2$, Y is CN and when X is NHCN, Y is H;
or a pharmaceutically acceptable salt thereof.

DETAILED DESCRIPTION OF THE INVENTION

The preparation of all the compounds of Formula (I), except of the compounds of Formula (IA), is known. All the compounds of Formula (I) are useful in treating a 5-lipoxygenase pathway mediated disease in an animal in need thereof by inhibiting the 5-lipoxygenase pathway in such animal.

Lombardino et al., U.S. Pat. No. 3,772,441, issued Nov. 13, 1973, the disclosure of which is hereby incorporated by reference, disclose preparation of compounds of the formula

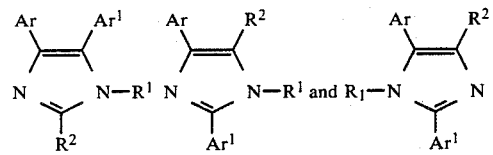

and the pharmaceutically acceptable acid addition salt thereof, wherein:
Ar and Ar¹ are each selected from furyl, thienyl, pyridyl, phenyl and substituted phenyl, wherein said substituents are selected from fluoro, chloro, bromo, and C$_{1-4}$ alkoxy;
R¹ is selected from H or C$_{1-4}$ alkyl; and
R² is selected from trifluoro methyl, C$_{1-4}$ alkyl, furyl, thienyl, pyridyl, and substituted phenyl wherein said substituents are selected from fluoro, chloro, bromo, or C$_{1-4}$ alkoxy.

Lombardino et al., J. Med. Chem., 17(11), 1182–1188 (1974), the disclosure of which is hereby incorporated by reference, disclose the preparation of compounds of the formula

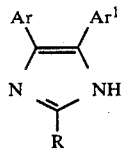

wherein Ar and Ar¹ are selected from methoxyphenyl, 4-ethoxyphenyl, 2-pyridyl and 4-halophenyl; and R is selected from 4-halophenyl, CF$_3$, phenyl and 4-methoxyphenyl.

Bender et al., J. Med. Chem., 28, 1169–1177 (1985), the disclosure of which is hereby incorporated by reference, disclosure the preparation of compounds of the formula

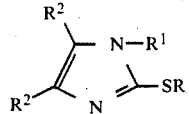

wherein R is methyl or ethyl, R¹ is H, methyl or ethyl, R² is 4-methoxyphenyl, and R³ is 4-methoxyphenyl, 4-bromophenyl or 3-fluorophenyl.

Cherkofsky et al., U.S. Pat. No. 4,190,666, issued Feb. 26, 1980, the disclosure of which is hereby incorporated by reference, disclose the preparation of compounds of the formula

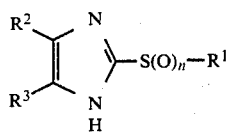

wherein:
n is 0, 1 or 2;
R$_1$ is C$_{1-6}$ alkyl or polyhalo C$_{1-6}$ alkyl; and
R$_2$ and R$_3$ are independently selected from monosubstituted phenyl wherein said substituent is selected from C$_{1-4}$ alkoxy, chloro or fluoro, and pharmaceutically acceptable salts thereof.

Zauer et al., Chem. Ber., 106, 1628–1636 (1973), the disclosure of which is hereby incorporated by reference, disclose the preparation of 4,5-bis(p-chlorophenyl)-2-(methylthio)imidazole and 4,5-bis(p-methoxypheny)-2-methylimidazole.

Ferrini et al., U.S. Pat. No. 4,308,277, issued Dec. 29, 1981, the disclosure of which is hereby incorporated by reference, disclose the preparation of compounds of the formula

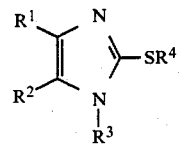

wherein:
R$_1$ and R$_2$ are independently selected from thienyl or monosubstituted phenyl wherein said substituents are selected from lower alkoxy and halo;
R$^3$ is H or lower alkyl; and
R$^4$ is lower alkyl;
and pharmaceutically acceptable salts thereof.

Dupont, Belgian patent application No. 845,074, published Nov. 2, 1977, the disclosure of which is hereby incorporated by reference, disclose the preparation of compounds of the formula

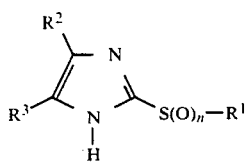

wherein:

n is 0, 1 or 2;

$R_1$ is mono or polyhalo $C_{1-4}$ alkyl or $C_{1-4}$ alkyl; and $R_2$ and $R_3$ are independently selected from mono-substituted phenyl wherein said substituents are selected from $C_{1-4}$ alkoxy, chloro or fluoro, and pharmaceutically acceptable salts thereof.

Janino et al., *Bulletin of the Chemical Society of Japan*, 45, 1474–1480 (1972), and White et al., *J. Org. Chem.*, 29, 1926–1930 (1964), the disclosure of both of which is hereby incorporated by reference, disclose the preparation of 2,4,5-tri(p-chloropheny)imidazole.

Cherkofsky et al., U.S. Pat. No. 4,182,769, issued Jan. 8, 1980, the disclosure of which is hereby incorporated by reference, disclose the preparation of compounds of the formula

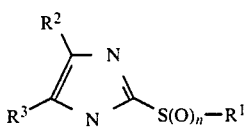

wherein:

n is 0, 1 or 2;

$R_1$ is $C_{1-6}$ alkyl and mono- and polyhalo $C_{1-4}$ alkyl; and $R_2$ and $R_3$ are independently selected from mono-substituted phenyl wherein said substituent is selected from $C_{1-4}$ alkoxy, Cl or F, and pharmaceutically acceptable salts thereof.

Ferrini et al., U.S. Pat. No. 4,461,770, issued July 24, 1984, the disclosure of which is hereby incorporated by reference, disclose the preparation of compounds of the formula

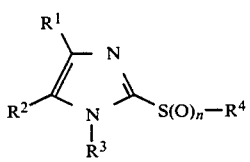

wherein at least one of the radicals $R_1$ and $R_2$ is a substituted or unsubstituted heteroaryl group and the other is a substituted or unsubstituted aryl group; $R_3$ is H or lower alkyl, n is 0, 1 or 2, and $R_4$ is a substituted or unsubstituted auphatic hydrocarbon radical, and pharmaceutically usable salts thereof.

Cherkofsky et al., U.S. Pat. No. 4,159,338, issued June 26, 1979, the disclosure of which is hereby incorporated by reference, disclose the preparation of compounds of the formula

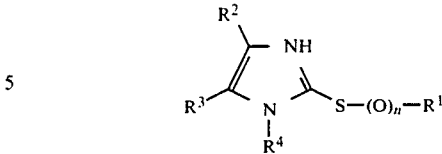

wherein:

n is 0, 1 or 2;

$R_1$ is polyfluoro $C_{1-2}$ alkyl;

$R_2$ and $R_3$ are independently selected from 2-thienyl, 3-thienyl, 3-pyridyl, 2-furyl or monosubstituted phenyl wherein said substituent is selected from $C_{1-4}$ alkoxy, Cl or F; and $R_4$ is H, and pharmaceutically acceptable acid addition salts thereof.

Bender et al., U.S. Pat. No. 4,175,127, issued Nov. 20, 1979, the disclosure of which is hereby incorporated by reference, disclose the preparation of compounds of the formula

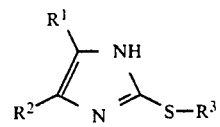

wherein:

$R_3$ is H, $C_{1-6}$ alkyl or mono- or polyhalo $C_{1-4}$ alkyl; and $R^1$ and $R^2$ are the same or different, but one of which always being pyridyl, are pyridyl or monosubstituted phenyl wherein said substituent is selected from lower alkoxy, chloro, fluoro or bromo.

Fitzi, et al., U.S. Pat. No. 3,940,486, issued Feb. 24, 1976, and Fitzi, et al., U.S. Pat. No. 3,929,807, issued Dec. 30, 1975, the disclosure of both of which is hereby incorporated by reference, disclose the preparation of compounds of the formula

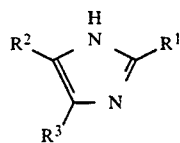

wherein:

$R_1$ is halo-substituted phenyl; and one of the groups $R_2$ and $R_3$ represents phenyl which is optionally substituted by halo or lower alkoxy and the other is a 6-membered heteroaromatic ring, and salts of such compounds.

Lantos, et al., *J. Med. Chem.*, 27(1), 72–75 (1984), the disclosure of which is hereby incorporated by reference disclose of which is hereby incorporated by reference disclose the preparation of 4-(4-methoxyphenyl)-5-(4-pyridyl)-2-thione-imidazole and 4-(4-fluorophenyl)-5-(4-pyridyl)-2-thione-imidazole.

The preparation of the compounds of Formula (IA) is accomplished by treatment of 1 equivalent of a 2-bromo-1,2-diaryl(heteroaryl)ethan-1-one in a suitable unreactive solvent, such as dimethyl formamide (DMF), with three equivalents or cyanoguanidine. The 2-bromo-1,2-diaryl(heteroaryl)-ethan-1-one starting materials are prepared by treatment of the corresponding 1,2-diary(heteroaryl)ethan-1-ones with a brominating agent such as bromine or pyridinium bromide perbromide. The ethanone starting materials are prepared by the methods described in Bender, et al., *J. Med. Chem.*, 28, 1169-1177 (1985), Brust, et al., Belgiam Pat. No. 668,701; *Chem. Abstr.*, 65, 5446c (1966), Cherkofsky, et al., U.S. Pat. No. 4,119, 592, and Fitzi, U.S. Pat. No. 3,940,486. These methods include acylation and picolyl sodium by an aryl or heteroaryl carboxylic acid ester, alkoxide catalyzed condensation of a heteroaryl carboxylic acid ester with an aryl acetic acid ester or arylacetonitrile, Friedel Crafts acylation of a substituted benzene by an aryl acetic acmid chloride reduction of a benzoin with tin and HCl, and Curtius rearrangement of azide of the stilbene carboxilic acid resulting from perkin condensation of a benzaldehyde with a phenylacetic acid ester.

Pharmaceutically acceptable salts and their preparation are well known to those skilled in pharmaceuticals. Preparation of some pharmaceutically acceptable salts of compounds of Formula (I) is disclosed by Lombardino et al., U.S. Pat. No. 3,772,441; Cherkofsky, et al., U.S. Pat. No. 4,190,666; Ferrini, et al., U.S. Pat. No. 4,308,277; Dupont, Belgian patent application No. 845,074; Cherkofsky et al., U.S. Pat. No. 4,182,769; Ferrini et al., U.S. Pat. No. 4,461,770; Cherkofsky et al., U.S. Pat. No. 4,159,338; Fitzi, et al., U.S. Pat. No. 3,940,486; and Fitzi, et al., U.S. Pat. No. 3,929,807; all of which are cited above. Preferred pharmaceutically acceptable salts of the compounds of Formula (I) include hydrochloride and hydrobromide salts.

The compounds of Formula (I) which are preferred for their ability to inhibit 5-lipoxygenase pathway, as evidenced by their ability to inhibit 5-lipoxygenase pathway products, such as $LTB_4$, 5-HETE and/or $LTC_4$, include those listed in Table A below:

TABLE A

FORMULA (I)

| Compound Number | R | $R^1$ | X | Y |
|---|---|---|---|---|
| 1 | 4-methoxyphenyl | 4-methoxyphenyl | S—$CH_3$ | $CH_3$ |
| 2 | 4-fluorophenyl | 4-fluorophenyl | $SO_2CF_2CF_2H$ | H |
| 3 | 4-methoxyphenyl | 4-methoxyphenyl | S—$CH_2CH_3$ | $CH_2CH_3$ |
| 4 | 4-methoxyphenyl | 4-methoxyphenyl | NH—CN($NH_2$) | H(CN) |
| 5 | 4-fluorophenyl | 4-fluorophenyl | NH—CN($NH_2$) | H(CN) |
| 6 | 4-methoxyphenyl | 4-methoxyphenyl | trifluoromethyl | H |
| 7 | 4-fluorophenyl | 4-fluorophenyl | 4-fluorophenyl | H |
| 8 | 4-pyridyl | 4-fluorophenyl | S | H |
| 9 | 4-pyridyl | 4-fluorophenyl | $SCF_2CF_2H$ | H |

It is known that some of the compounds of Formula (I) are useful for treating cyclooxygenase product-mediated disease states. It has now been discovered that all of the compounds of Formula (I) are also useful for treating disease states mediated by 5-lipoxygenase products by inhibiting the 5-lipoxygenase pathway. The discovery that the compounds of Formula (I) are dual inhibitors of the cyclooxygenase and 5-lipoxygenase pathways or sole inhibitors of the 5-lipoxygenase pathway is based on the effects of the compounds of Formula (I) on tissue inflammation in vivo and on the production of 5-lipoxygenase products by inflammatory cells in vitro in assays which are described in the Examples. In summary, such assays reveal that the compounds of Formula (I) display anti-inflammatory activity in arachidonic acid-induced inflammation in the mouse ear model. The cyclooxygenase inhibitor, indomethacin, did not reduce inflammation or cell infiltration in this assay. These data, together with previous observations on the anti-edematous effects of the compounds of Formula (I) in inflammatory lesions caused by cyclooxygenase-generated products, reveal that the compounds of Formula (I) inhibit either just the 5-lipoxygenase pathway or both the 5-lipoxygenase and cyclooxygenase pathways of arachidonic acid metabolism. The 5-lipoxygenase pathway inhibitory action of the compounds of Formula (I) was confirmed by showing that they impaired the production of 5-lipoxygenase products such as leukotriene $B_4$ (di-HETE) and 5-HETE production by RBL-1 cells.

The pathophysiological role of arachidonic acid metabolites has been the focus of recent intensive studies. In addition to the well-described phlogistic activity (i.e. general inflammatory activity) of prostaglandins, the more recent description of similar activity for eicosanoids has broadened the interest in these products as mediators of inflammation [See, O'Flaherty, *Lab. Invest.*, 47, 314-329 (1982)]. The reported discovery of potent chemotactic and algesic activity for $LTB_4$ [see, Smith, *Gen. Pharmacol.*, 12, 211-216 (1981) and Levine et al., *Science*, 225, 743-745 (1984)], together with known $LTC_4$ and $LTD_4$-mediated increase in capillary permeability [see, Simmons et al., *Biochem. Pharmacol.*, 32, 1353-1359 (1983), Veno et al., *Prostaglandins*, 21, 637-647 (1981), and Camp et al., *Br. J. Pharmacol.*, 80, 497-502 (1983)], has led to their consideration as targets for pharmacological intervention in both the fluid and cellular phases of inflammatory diseases.

The pharmacology of several inflammatory model systems has attested to the effectiveness of corticosteroids in reducing the cellular infiltration. These results, and the observation that corticosteroids inihibit the generation of both cyclooxygenase and lipoxygenase products, suggest that such dual inhibitors may effectively reduce both the fluid and cellular phases of the inflammatory response since selective cyclooxygenase inhibitors do not reliably inhibit cell influx into inflammatory sites [See, Vinegar et al., *Fed. Proc.*, 35, 2447-2456 (1976), Higgs et al., *Brit. Bull.*, 39, 265-270 (1983), and Higgs et al., *Prostaglandins, Leukotrienes and Medicine*, 13, 89-92 (1984)]. The observations outlined above cogently argue that a dual inhibitor of arachidonic acid metabolism would be a more effective antiinflammatory agent than an inhibitor of cyclooxygenase only. Under optimal conditions, it is likely that an agent with preferential lipoxygenase inhibitory activity would not share the ulcerogenic liability of cyclooxygenase inhibitors or the toxicity of corticosteroids.

Recent clinical data also support the enthusiasm for inhibitors of the 5-lipoxygenase pathway of arachidonic acid metabolism in a variety of inflammatory diseases in which granulocyte and/or monocyte infiltration is prominent. The reported demonstration of elevated levels of $LTB_4$ in rheumatoid arthritic joint fluid [See, Davidson et al., *Ann. Rheum. Dis.*, 42, 677–679 (1983)] also suggests a contributing role for arachidonic acid metabolites in rheumatoid arthritis. The recently reported preliminary observation of efficacy, including remission, reported with sulfasalazine treatment of rheumatoid arthritic patients [See Neumann et al., *Brit. Med. J.*, 287, 1099–1102 (1983)] illustrates the utility of inhibitors of the 5-lipoxygenase pathway in rheumatoid arthritis.

Sulfasalazine, which is used for treatment of ulcerative colitis, has been reported to inhibit $LTB_4$ and 5-HETE production in vitro [See, Stenson st al., *J. Clin. Invest.*, 69, 494–497 (1982)]. This observation, coupled with the fact that it has been reported that inflamed gastrointestinal mucosa from inflammatory bowel disease patients showed increased production of $LTB_4$ [See, Sharon et al., *Gastroenterol.*, 84, 1306 (1983)], suggests that sulfasalazine can be effective by virtue of inhibition of production of chemotactic eicosanoids (such as the 5-lipoxygenase pathway product known as $LTB_4$). The observations serve to underscore utility of inhibitors of the 5-lipoxygenase pathway in inflammatory bowel disease.

Anothr area of utility for an inhibitor of the 5-lipoxygenase pathway is in the treatment of psoriasis. It was demonstrated that involved psoriatic skin had elevated levels of $LTB_4$ [See, Brain et al., *Lancet*, 19, Feb. 19, 1983]. The promising effect of benoxaprofen on psoriasis [See, Allen et al., *Brit. J. Dermatol.*, 109, 126–129 (1983)], a compound with in vitro lipoxygenase inhibitory activity on psoriasis, lends support to the concept that such inhibitors can be useful in the treatment of psoriasis.

Lipoxygenase products have been identified in exudate fluids from gouty patients. This disorder is characterized by massive neutrophil infiltration during the acute inflammatory phases of the disease. Since a major 5-lipoxygenase product, $LTB_4$, is produced by neutrophils, it follows that inhibition of the synthesis of $LTB_4$ can block an amplification mechanism in gout.

Another area in which inhibitors of the 5-lipoxygenase pathway can have utility is in myocardial infarction. Studies in dogs with the dual cyclooxygenase lipoxygenase, inhibitor, BW755-C, demonstrated that the area of infarction following coronary occlusion was reduced, and such reduction was attributed to inhibition of leukocyte infiltration into the ischaemic tissue [See, Mollane et al., *J. Pharmacol. Exp. Therap.*, 228, 510–522 (1984)].

Yet another area of utility for inhibitors of the 5-lipoxygenase pathway is in the area of prevention of rejection of organ transplants. [See, e.g., Foegh et al., *Adv. Prostaglandin, Thromboxane, and Leukotriene Research*, 13, 209–217 (1983)]

Yet another utility for inhibitors of the 5-lipoxygenase pathway is in the treatment of tissue trauma. [See, e.g., Denzlinger et al., *Science*, 230 (4723), 330–332 (1985)].

Furthermore, another area of utility for inhibitors of the 5-lipoxygenase pathway is in the treatment of inflammatory reaction in the central nervous system, including multiple sclerosis. [See, e.g., MacKay, et al., *Clin. Exp. Immunol.*, 15, 471–482 (1973)].

Another area of utility for inhibitors of the 5-lipoxygenase pathway is in the treatment of asthma. [See, e.g., Ford-Hutchinson, *J. Allergy Clin. Immunol.*, 74, 437–440 (1984)].

This invention relates to a pharmaceutical composition comprising an effective, 5-lipoxygenase product inhibiting amount of a compound of Formula (IA), or a pharmaceutically acceptable salt thereof, and a pharmaceutically acceptable carrier or diluent. As stated above, it will be apparent to one of skill in the art that all the compounds of Formula (IA) are within the scope of Formula (I).

The compounds of Formula (I) are administered in conventional dosage forms prepared by combining a compound of Formula (I) ("active ingredient") or a salt thereof in an amount sufficient to produce activity with a standard pharmaceutical carrier according to conventional procedures. These procedures may involve mixing, granulating and compressing or dissolving the ingredients as appropriate to the desired preparation. The resulting pharmaceutical compositions containing an effective 5-lipoxygenase pathway inhibiting amount of a compound of Formula (IA) are also objectives of this invention. invention.

The pharmaceutical carrier employed may be, for example, either a solid or liquid. Examplary of solid carriers are lactose, terra alba, sucrose, talc, gelatin, agar, pectin, acacia, magnesium stearate, stearic acid and the like. Examplary of liquid carriers are syrup, peanut oil, olive oil, water and the like. Similarly, the carrier or diluent may include a time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 50 mg to about 500 mg. If a liquid carrier is used, the preparation will be in the form of a syrup, emulsion, soft gelatin capsule, sterile injectable liquid such as an ampule or a nonaqueous liquid suspension.

To obtain a stable water soluble dose form, a pharmaceutically acceptable acid addition salt, preferably hydrochloride or sulfate, of a compound of Formula (I) is dissolved in an aqueous solution of an organic or morganic acid, such as a 0.3M solution of succinic acid or preferably citric acid. In addition to sulfate and hydrochloride, methanesulfonate, phosphate and hydrobromide are exemplary of other water soluble salts.

Preferably, each parenteral dosage unit will contain the active ingredient in an amount of from about 50 mg to about 500 mg.

The compounds of Formula (I) may also be administered by inhalation. Appropriate dosage forms for such administration, such as an aerosol formulation or a metered dose inhaler, may be prepared by convention techniques. The preferred daily dose amount of a compound of Formula (I) administered by inhalation as from about 10 mg to about 200 mg per day.

The compounds of Formula (I) may be administered topically to a mammal in need of the inhibition of the 5-lipoxygenase pathway of arachidonic acid metabolism. Thus, the compounds of Formula (I) may be administered topically in the treatment or prophylaxis of inflammation in an animal, including man and other mammals, and may be used in the relief or prophylaxis of 5-lipoxygenase pathway mediated diseases, such as rheumatoid arthritis, rheumatoid spondylitis, oestoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of Formula (I) (hereinafter referred to as the active ingredient) required for therapeutic effect on topical administration will, of course, vary with the compound chosen, the nature and severity of the inflammatory condition and the animal undergoing treatment, and is ultimately at the discretion of the physician. A suitable anti-inflammatory dose of an active ingredient is 1 $\mu$g to 500 mg of base for topical administration, the most preferred dosage being 1 $\mu$g to 1000 $\mu$g, for example, 5 to 25 $\mu$g; administered two or three times daily.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intrasmuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops.

Lotions or liniments for application to the skin may also include an agent to hasten drying and to cool the skin, such as an alcohol or acetone, and/or a moisturizer such as glycerol or an oil such as caster oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil or natural origin such as almond, corn, arachis, castor or olive oil; wool fat or its derivatives, or a fatty acid such as steric or oleic acid together with an alcohol such as prolylene glycol or macrogols. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

This invention relates to a method of treating a disease state mediated by the 5-lipoxygenase pathway in an animal in need thereof, including humans and other mammals, provided that such animal is in need of treatment of a 5-lipoxygenase pathway mediated disease other than, or in addition to, rheumatoid arthritis, which comprises administering to such animal an effective, 5-lipoxygenase pathway inhibiting amount of a Formula (I) compound. By "treating" is meant either prophylactive or therapeutic therapy. By "mediated" is meant exacerbated or caused by. This invention also relates to a method of treating rheumatoid arthritis in an animal in need thereof, including humans and other mammals, which comprises administering to such animal an effective, 5-lipoxygenase pathway inhibiting amount of a Formula (IA) compound. The Formula (I) compound is administered to an animal in need of inhibition of the 5-lipoxygenase pathway in an amount sufficient to inhibit the 5-lipoxygenase pathway. The Formula (IA) compound is administered to an animal in need of treatment of rheumatoid arthritis to an animal in need of treatment of rheumatoid arthritis in an amount sufficient to inhibit the 5-lipoxygenase pathway. Such formula (I) compound can be administered to such animal in a conventional dosage form prepared by combining the Formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The route of administration may be parenteral by inhalation or topical. The compounds of Formula (I) are either poorly active or inactive when administered orally. The term perenteral as used herein includes intravenous, intramuscular, subcutaneous, intranasal, intravaginal, intrarectal or intraperitoneal administration. The subcutaneous and intramuscular forms of parenteral administration are generally preferred. The daily dosage regimen will preferably be from about 50 mg to about 1000 mg per day.

It will be recognized by one of skill in the art that the optimal quantity and spacing of individual dosages of the Formula (I) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (I) compound given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following examples are, therefore, to be construed as merely illustrative and not a limitation of the scope of the present invention in any way.

SYNTHESIS EXAMPLES

Example 1

4,5-Bis(4-fluorophenyl)-2-cyanamido-imidazole or 4,5-Bis(4-fluorophenyl)-2-amino-1-cyano-imidazole To a solution of 15 g (0.048 mol) of 2-bromo-1,2-di-(4-fluorophenyl)-ethan-1-one in 80 ml of dry DMF was added 12.1 g. (0.144 mol) of cyanoguanidine with stirring. After 120 hours, the solution was poured into cold water and extracted into methylene chloride. The extract was washed with water, dried ($MgSO_4$) and concentrated. The chilled concentrate deposited a solid which was filtered and recrystallized from acetonitrile to afford white crystals, melting point (mp) 197°–199° C.

Analyzed for $C_{16}H_{10}F_2N_4$; Calcd.: C, 64,86; H, 3.40; N, 18.91. Found: C, 64.90; H, 3.57; N, 18.71.

Example 2

4,5-Bis(4-methoxyphenyl)-2-cyanamido-imidazole or 4,5-Bis(4-methoxyphenyl)-2-amino-1-cyano-imidazole To a solution of 25 g (0.074 mol) of 2-bromoanisoin in 150 ml of dry DMF was added 18.75 g (0.223 mol) of cyanoguanidine with stirring. After 96 hours, the solution was poured into 500 ml of cold water. The mixture was made acidic with 6N HCl and extracted with methylene chloride. The organic layer was washed with water, dried ($MgSO_4$) and concentrated to give a yellow solid. Recrystallization from methanol-water gave white crystals, melting point 192°–199° C.

Analyzed for $C_{18}H_{16}N_4O_2$; Calcd.: C, 67.49; H, 5.03; N, 17.49. Found: C, 67.44; H, 4.79; N, 17.43.

UTILITY EXAMPLES

In the following Examples male Balb/c mice (20–28 g) were used. All mice were obtained from Charles River Breeding Laboratories, Kingston, N.Y. Within a single experiment, mice were sex and age matched.

In the following Examples, reagents used were employed as follows:

The compounds of Formula (I), indomethacin, naproxen, and ibuprofen were each used as the free base. The compounds were homogenized in 0.5% tagacanth. Compounds were administered by gavage at the indicated dose in a final volume of 10 ml/kg. The compounds of Formula (I) were solubilized in dimethylacetamide and diluted with olive oil for subcantaneous administration.

For in vitro experiments, compounds were dissolved at appropriate concentrations in ethanol (final concentration $\mu 1.0\%$) and then diluted to final concentrations using the buffers indicated in the text.

I.

METHODS

Arachidonic Acid-induced Mouse Ear Inflammation

Arachidonic acid in acetone (2 mg/20 μl) was applied to the inner surface of the left ear. The thickness of both ears was then measured with a dial micrometer one hour after treatment, and the dial were expressed as the change in thickness ($10^{-3}$ cm) between treated and untreated ears.

Test compounds were given orally in 0.5% tragacanth at the times indicated in the text prior to the topical application of arachidonic acid.

Parenteral administration of compound was accomplished by subcutaneous injection of solution as indicated.

Assay of 5-lipoxygenase and Cyclooxygenase Activities

The activities of these enzymes in extracts of RBL-1 cells were assayed using the method of Jakschik and Lee, Nature, 287, 51–52 (1980). RBL-1 cells were obtained from the American Type Culture Collection (#CRL 1378) and were grown at 37° C. (5% $CO_2$ in air) in spinner culture in MEM supplemented with 10% heat inactivated fetal calf serum. Harvested cells were washed with 50 mM sodium phosphate buffer, pH 7.0, containing 1 mM EDTA and 0.1% galatin, resuspended in fresh buffer ($5 \times 10^7$ cells/ml) and disrupted by nitrogen cavitation using the Parr bomb at 750 psi for 10 min. The broken cell extract was then centrifuged at $10,000 \times g$ for 60 minutes (min). Aliquots (0.25 mls) of the supernatant were preincubated with or without drugs for 10 min, after which 10 μl $CaCl_2$ (2 mM) of 2.5 mM arachidonic acid-1-$^{14}C$ (final concentration was 25M; specific activity 20,000 dpm/nmole). After incubation for 5 min at 5° C., the reaction was terminated by addition of 2 volumes (0.5 ml) ice cold acetone and the sample was allowed to deproteinize on ice for 10 min prior to centrifugation at $1,000 \times g$ for 10 min. The deproteinized supernatant was adjusted to pH 3.5 with 2N formic acid and extracted with 2 volumes of ice cold ethyl acetate. The extracted samples were dried under argon, redissolved in ethyl acetate and applied to Whatman LK5D thin layer chromatography (TLC) plates which were developed using the A-9 solvent system [organic phase of ethyl acetate:2,2,5-trimethylpentane:acetic acid:water (110:50:20:10)] described by Hamberg and Samuelsson, J. Bio. Chem., 241, 257–263 (1966). Arachidonic acid, 5-HETE, $LTB_4$ and $PGD_2$ were quantified with a Berthold LB 2832 autoscanner.

Drug-induced effects on enzyme activities are described as the concentration of drug causing a 50% inhibition of metabolite synthesis ($IC_{50}$).

LTC-4 Production of Human Monocytes

One of the compounds of Formula (I), i.e., Compound Number 8 from Table 1, was evaluated for its ability to inhibit the production of $LTC_4$ by human monocytes according to the following protocol.

Human monocytes were prepared from whole blood supplied by the American Red Cross. The blood was fractionated by a two-step procedure employing sedimentation on Ficoll followed by sedimentation on Percoll. The mononuclear cell fraction recovered was composed of 80–90% monocytes with the remainder of the cells being predominant lymphocytes. The monocytes were plated at $1 \times 10^6$ cells per well in a Costar 24 well tissue culture plat and allowed to adhere for one hour at 37° C. Non-adherent cells were removed by washing. The cells were stimulated with 1M of A23187 calcium ionophore for 3 hours at 37° C. to induce LTC-4 produced when drugs were evaluated. They were added to the cells 30 minutes prior to the A23187. Supernatants were collected, clarified by centrifugation and store frozed at −20° C. until assay. The LTC-4 content was determined by using a New England Nuclear Leukotriene C-4 ($^3$H) RIA Kit as per instructions.

II.

RESULTS

The Effect of Compounds of Formula (I) on Arachidonic Acid-Induced Inflammation Elucidation of the antiinflammatory activity of compounds of Formula (I) was achieved in models of arachidonic acid-induced edema in mice and rats. The mouse ear edematous response to arachidonic acid has been shown to be sensitive to agents that inhibit both lipoxygenase- and cyclooxygenase-generated mediators or that selectively inhibit lipoxygenase, but not cyclooxygenase, enzyme activity [See, Young et al., J. Invest. Dermatol., 82, 367-371 (1984)]. Compounds of Formula (I) produced marked inhibition of the edematous response normally seen 1 hour after the application of 2 mg of arachidonic acid to the ear (Table I). The cyclooxygenase inhibitors, indomethacin (10 mg/kg, p.o.), ibuprofen (250 mg/kg, p.o.) and naproxen (100 mg/kg, p.o.) did not exhibit detectable antiinflammatory activity in this assay, despite use to near maximally tolerated doses.

Collectively, these findings indicate that compounds of Formula (I) are, in general, potent inhibitors of the inflammatory response to arachidonic acid was also inhibited by agents that inhibit lipoxygenase activity but not by selective cyclooxygenase inhibitors.

The Effect of Compounds of Formula (I) on Arachidonic Acid Metabolism

Experiments using a soluble extract preparation of RBL-1 cells containing only lipoxygenase activity. confirmed the inhibitory effects of compounds of Formula (I) on $LTB_4$ production (Table II) and 5-HETE production (Table III). The data in Table II shows that compounds of Formula (I) are able to inhibit the 5-lipoxygenase pathway since they inhibit production of $LTB_4$, a 5-lipoxygenase pathway product. Indomethacin at concentrations up to $10^{-4}$M was inactive. The data in Table III also shows that compounds of Formula (I) are able to inhibit the 5-lipoxygenase pathway since they inhibit production of 5-HETE, a 5-lipoxygenase pathway product.

$LTD_4$ Inhibition Assay

As shown in Table 4, a compound of Formula (I) was efficacious in inhibiting $LTC_4$ production, a 5-lipoxygenase pathway product, by human monocytes. These data confirm the ability of compounds of Formula (I) to inhibit the 5-lipoxygenase pathway.

As seen in Table 1 not all compounds of Formula (I) significantly inhibited arachidonic acid-induced ear swelling, but such compounds did significantly inhibit the production of $LTB_4$ by RBL-1 high speed supernatant (Table II) and/or the production of 5-HETE (Table III) indicating that such compounds are indeed inhibitors of the 5-lipoxygenase pathway.

TABLE I

The Effect of Compounds of Formula (I) on Arachidonic Acid - Induced Ear Swelling

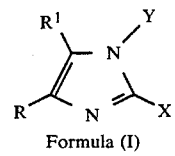

Formula (I)

| Compound Number | R | $R^1$ | X | Y | % Inhibition of Ear Swelling[a,b] |
|---|---|---|---|---|---|
| 1 | 4-methoxyphenyl | 4-methoxyphenyl | S—$CH_3$ | $CH_3$ | 51*** |
| 2 | 4-fluorophenyl | 4-fluorophenyl | $SO_2CF_2CF_2H$ | H | 41*** |
| 3 | 4-methoxyphenyl | 4-methoxyphenyl | S—$CH_2CH_3$ | $CH_2CH_3$ | NS |
| 4 | 4-methoxyphenyl | 4-methoxyphenyl | NH—CN ($NH_2$) | H (CN) | 46*** |
| 5 | 4-fluorophenyl | 4-fluorophenyl | NH—CN ($NH_2$) | H (CN) | 59*** |
| 6 | 4-methoxyphenyl | 4-methoxyphenyl | trifluoromethyl | | 28** (p.o.) |
| 7 | 4-fluorophenyl | 4-fluorophenyl | 4-fluorophenyl | H | 15* |
| 8 | 4-pyridyl | 4-fluorophenyl | S | H | NT |
| 9 | 4-pyridyl | 4-fluorophenyl | $SCF_2CF_2H$ | H | NT |

[a] Screened at 50 mg/kg s.c. or i.p. unless indicated as oral dosing (p.o.)
[b] * = p μ.05,  = p μ.01, * = p μ.001, NS = not significant.

TABLE II

The Effect of Compounds of Formula (I) on 5-LO Activity (LTB$_4$ Production)

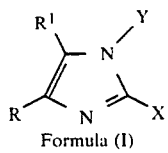

Formula (I)

| Compound Number | R | R$^1$ | X | Y | 5LO$^a$ IC$_{50}$ ($\mu$M) |
|---|---|---|---|---|---|
| 1 | 4-methoxyphenyl | 4-methoxyphenyl | S—CH$_3$ | CH$_3$ | 13.0 |
| 2 | 4-fluorophenyl | 4-methoxyphenyl | SO$_2$CF$_2$H | H | 6.6 |
| 3 | 4-methoxyphenyl | 4-methoxyphenyl | S—CH$_2$CH$_3$ | CH$_2$CH$_3$ | 8.4 |
| 4 | 4-methoxyphenyl | 4-methoxyphenyl | NH—CN (NH$_2$) | H (CN) | 1.5 |
| 5 | 4-fluorophenyl | 4-fluorophenyl | NH—CN (NH$_2$) | H (CN) | 1.0 |
| 6 | 4-methoxyphenyl | 4-methoxyphenyl | trifluoromethyl | H | 1.1 |
| 7 | 4-fluorophenyl | 4-fluorophenyl | 4-fluorophenyl | H | 10.0 |
| 8 | 4-pyridyl | 4-fluorophenyl | S | H | 1.5 |
| 9 | 4-pyridyl | 4-fluorophenyl | SCF$_2$CF$_2$H | H | NT |

$^a$IC$_{50}$ determined on LTB$_4$ production by RBL-1 high speed supernatant.
$^b$NT = not tested.

TABLE III

The Effect of Compounds of Formula (I) on 5-HETE Production

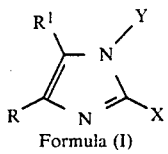

Formula (I)

| Compound Number | R | R$^1$ | X | Y | 5LO$^a$ IC$_{50}$ ($\mu$M) |
|---|---|---|---|---|---|
| 1 | 4-methoxyphenyl | 4-methoxyphenyl | S—CH$_3$ | CH$_3$ | 13 |
| 2 | 4-fluorophenyl | 4-fluorophenyl | SO$_2$CF$_2$H | H | 16 |
| 3 | 4-methoxyphenyl | 4-methoxyphenyl | S—CH$_2$CH$_3$ | CH$_2$CH$_3$ | 10.4 |
| 4 | 4-methoxyphenyl | 4-methoxyphenyl | NH—CN (NH$_2$) | H (CN) | 3.1 |
| 5 | 4-fluorophenyl | 4-fluorophenyl | NH—CN (NH$_2$) | H (CN) | 8 |
| 6 | 4-methoxyphenyl | 4-methoxyphenyl | trifluoromethyl | H | .7 |
| 7 | 4-fluorophenyl | 4-fluorophenyl | 4-fluorophenyl | H | 10 |
| 8 | 4-pyridyl | 4-fluorophenyl | S | H | 17 |
| 9 | 4-pyridyl | 4-fluorophenyl | SCF$_2$CF$_2$H | H | 95 |

$^a$IC$_{50}$ determined on 5-HETE production by RBL-1 high speed supernatant.

TABLE IV

The Effect of Compounds of Formula (I) on LTC$_4$ Production by Human Monocytes

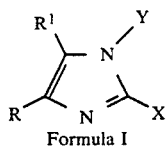

Formula I

| Compound Number | R | R$^1$ | X | Y | LTC$_4$$^a$ ($\mu$M) |
|---|---|---|---|---|---|
| 8 | 4-pyridyl | 4-fluorophenyl | S | H | .8 |

$^a$IC$_{50}$ determined on LTB$_4$ production by human monocytes.

EXAMPLE A

Injectable Parenteral Composition

A pharmaceutical composition of this invention in a form suitable for administration by injection is prepared by stirring 1.5% by wright of a compound of Formula (IA) in 10% by volume propylene glycol and water. The solution is sterilized by filtration.

EXAMPLE B

Ointment Composition

Compound of Formula (IA) 1.0 g
White soft paraffin to 100.0 g.

The compound of Formula (IA) is dispersed in a small volume of the vehicle. This dispersion is gradually incorporated into the bulk to produce a smooth, homogenous product which is filled into collapsible metal tubes.

EXAMPLE C

Topical Cream Composition

Compound of Formula (IA) 1.0 g
Polawax GP 200 20.0 g
Lanolin Anhydrous 2.0 g
White Beeswax 2.5 g
Methyl hydroxybenzoate 0.1 g
Distilled Water to 100.0 g.

The polawax, beeswax and lanolin are heated together at 60° C. and a solution of methyl hydroxybenzoate is added. Homogenization is achieved using high speed stirring and the temperature is allowed to fall to 50° C. The compound of Formula (IA) is added and dispersed throughout, and the composition is allowed to cool with slow speed stirring.

EXAMPLE D

Topical Lotion Composition

Compound of Formula (1A) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml.

The methyl hydroxybenzoate and glycerin are dissolved in 70 ml of the water at 75°. The sorbitan monolaurate, polysorbate 20 and cetostearyl alcohol are melted together at 75° C. and added to the aqueous solution. The resulting emulsion is homogenized, allowed to cool with continuous stirring and the compound of Formula (IA) is added as a suspension in the remaining water. The whole suspension is stirred until homogenous.

EXAMPLE E

Eye Drop Composition

Compound of Formula (IA) 0.5 g
Methyl Hydroxybenzoate 0.01 g
Propyl Hydroxybenzoate 0.04 g
Purified Water B.P. to 100.00 ml.

The methyl and propyl hydroxybenzoates are dissolved in 70 ml purified water at 75° C. and the resulting solution is allowed to cool. The compound of Formula (IA) is then added, and the solution is made up to 100 ml with purified water. The solution is sterilized by filtration through a membrane filter (0.22 mu m pore size) and packed aseptically into suitable sterile containers.

EXAMPLE F

Composition For Administration by Inhalation

For an aerosol container with a capacity of 15–20 ml: Mix 10 mg of a compound of Formula (IA) with 0.1–0.2% of a lubricating agent, such as Span 85 or oleic acid, and disperse such mixture in a propellant (c.a.), such as freon, preferably a combination of freon 114 and freon 12, and put into an appropriate aerosol container adopted for either intranasal or oral inhalation administration.

EXAMPLE G

Composition for Administration by Inhalation

For an aerosol container with a capacity of 15–20 ml: Dissolve 10 mg of a compound of Formula (IA) in ethanol (6–8 ml) and 0.1–0.2% of a lubricating agent, such as Span 85 or oleic acid, and disperse such in a propellant (c.a.), such as freon, preferably a combination of freon 114 and freon 12, and put into an appropriate aerosol container adapted for either intranasal or oral inhalation administration.

What is claimed is:

1. A compound of the formula

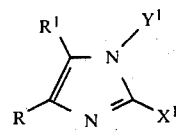

wherein:
$X^1$ is NHCN or $NH_2$;
$R^1$ and R are independently selected from 4-pyridyl or monosubstituted phenyl wherein said substituent is selected from halo or $C_{1-4}$ alkoxy; and
$Y^1$ is H or CN provided that when $X^1$ is $NH_2$, $Y^1$ is CN when $X^1$ is NHCN, $Y^1$ is H; or a pharmaceutically acceptable salt thereof.

2. The compound of claim 1 wherein $Y^1$ is H, $X^1$ is NHCN and R and $R^1$ are both 4-methoxyphenyl.

3. The compound of claim 1 wherein $Y^1$ is H, $X^1$ is NHCN and R and $R^1$ are both 4-fluorophenyl; or wherein $Y^1$ is CN, $X^1$ is $NH_2$ and R and $R^1$ are both 4-fluorophenyl.

4. A pharmaceutical composition having 5-lipoxygenase inhibitory activity comprising an effective, non-toxic 5-lipoxygenase pathway inhibiting amount of a compound of the formula

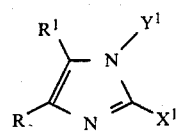

wherein:
$X^1$ is NHCN or $NH_2$;
$R^1$ and R are independently selected from 4-pyridyl or monosubstituted phenyl wherein said substituent is selected from halo or $C_{1-4}$ alkoxy; and
$Y^1$ is H or CN provided that when $X^1$ is $NH_2$, $Y^1$ is CN and when $X^1$ is NHCN, $Y^1$ is H; or a pharmaceutically acceptable salt or thereof, and a pharmaceutically acceptable carrier or diluent.

5. The composition of claim 4 wherein $Y^1$ is H, $X^1$ is NHCN and R and $R^1$ are both 4-methoxyphenyl.

6. The composition of claim 4 wherein $Y^1$ is H, $X^1$ is NHCN and R and $R^1$ are 4-fluorophenyl; or wherein $Y^1$ is CN, $X^1$ is $NH_2$ and R and $R^1$ are both 4-fluorophenyl.

7. The composition of claim 4 wherein the composition is in a dosage unit form adapted for parenteral administration.

8. The composition of claim 7 wherein the composition comprises the compound in an amount of from about 25 mg to about 200 mg.

9. The composition of claim 4 wherein the composition is in a dosage unit form adapted for administration of inhalation.

10. The composition of claim 4 wherein the composition is in a dosage unit form adapted for topical administration.

11. A method for treating rheumatoid arthritis in an animal in need thereof which comprises administering to such animal an effective, non-toxic 5-lipoxygenase pathway inhibiting amount of a compound of the formula

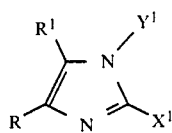

wherein:
X$^1$ is NHCN or NH$_2$;
R$^1$ and R are independently selected from 4-pyridyl or monosubstituted phenyl wherein said substituent is selected from halo or C$_{1-4}$ alkoxy; and
Y$^1$ is H or CN provided that when X$^1$ is NH$_2$, Y$^1$ is CN and when X$^1$ is NHCN, Y$^1$ is H; or a pharmaceutically acceptable salt thereof.

12. The method of claim 11 wherein Y$^1$ is H, X$^1$ is NHCN and R and R$^1$ are both 4-methoxyphenyl.

13. The method of claim 11 wherein Y$^1$ is H, X$^1$ is NHCN and R and R$^1$ are both 4-fluorophenyl; or wherein Y is CN, X is NH$_2$ and R and R$^1$ are both 4-fluorophenyl.

14. The method of claim 11 wherein the compound is administered parenterally.

15. The method of claim 14 wherein the amount of compound administered in a dosage unit is from about 25 mg to about 200 mg.

16. The method of claim 14 wherein the amount of compound administered per day is from about 50 mg to about 1000 mg.

17. The method of claim 14 wherein the compound is administered by inhalation.

18. The method of claim 17 wherein the amount of compound administered is from about 10 mg to about 200 mg per day.

19. The method of claim 14 wherein the compound is administered topically.

20. The method of claim 19 wherein the amount of compound administered per dose is 1 μg to 1000 μg.

21. A method of treating a 5-lipoxygenase pathway mediated disease in an animal in need thereof, provided that such animal is in need of treatment of a 5-lipoxygenase pathway mediated disease other than, or in addition to, rheumatoid arthritis, which comprises administering to such animal an effective, non-toxic 5-lipoxygenase pathway inhibiting amount of a compound of the formula,

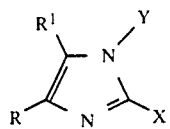

wherein:
X is S, S(0)$_n$R$^2$, NHCN, NH$_2$, polyhalo C$_{1-4}$ alkyl, or 4-halophenyl;
n is 0, 1 or 2;
R$^2$ is selected from H, C$_{1-6}$ alkyl, or mono- or polyhalo C$_{1-4}$ alkyl;
R and R$^1$ are independently selected from pyridyl or mono substituted phenyl wherein said substituent is selected from halo or C$_{1-4}$ alkoxy; provided that when R and/or R$^1$ are pyridyl, R$^2$ is other than C$_{1-6}$ alkyl, tetrahaloethyl or C$_{1-4}$ perhaloalkyl; and
Y is H, CN, or C$_{1-4}$ alkyl provided that when X is NH$_2$, Y is CN and when X is NHCN, Y is H; or a pharmaceutically acceptable salt thereof.

22. The method of claim 21 wherein the compound is administered parenterally.

23. The method of claim 22 wherein the amount of compound administered in a dosage unit is from amount 50 mg to about 500 mg.

24. The method of claim 22 wherein the amount of compound administered per day is from about 50 mg to about 1000 mg.

25. The method of claim 21 wherein the compound is administered by inhalation.

26. The method of claim 25 wherein the amount of compound administered is from about 10 mg to about 200 mg per day.

27. The method of claim 21 wherein the compound is administered topically.

28. The method of claim 27 wherein the amount of compound administered per dose is 1 μg to 1000 μg.

29. The method of claim 21 wherein R and R$^1$ are both 4-methoxyphenyl, X is 3—CH$_3$ and Y is CH$_3$.

30. The method of claim 21 wherein R and R$^1$ are both 4-fluorophenyl, X is SO$_2$CF$_2$CF$_2$H and Y is H.

31. The method of claim 21 wherein R and R$^1$ are both 4-methoxyphenyl, X is 3—CH$_2$CH$_3$ and Y is CH$_2$CH$_3$.

32. The method of claim 21 wherein R and R$^1$ are both 4-methoxyphenyl, X is NHCN and Y is H.

33. The method of claim 21 wherein R and R$^1$ are both 4-fluorophenyl, X is NHCN and Y is H; or wherein R and R$^1$ are both 4-fluorophenyl, X is NH$_2$ and Y is CN.

34. The method of claim 21 wherein R and R$^1$ are both 4-methoxyphenyl, X is trifluoromethyl and Y is H.

35. The method of claim 21 wherein R and R$^1$ are both 4-fluorophenyl, X is 4-fluorophenyl and Y is H.

36. The method of claim 21 wherein R is 4-pyridyl, R$^1$ is 4-fluorophenyl, X is S and Y is H.

37. The method of claim 21 wherein R is 4-pyridyl, R$^1$ is 4-fluorophenyl, X is SCF$_2$CF$_2$H and Y is H.

* * * * *